United States Patent
Righini et al.

(10) Patent No.: US 11,517,425 B2
(45) Date of Patent: Dec. 6, 2022

(54) DEVICE FOR IMPLANTING A PROSTHESIS FOR A HEART VALVE AND ASSEMBLY PROCEDURE

(71) Applicants: Giovanni Righini, Gland (CH); Cindy Trinh, San Marcos, CA (US); Dong Ik Shin, Poway, CA (US)

(72) Inventors: Giovanni Righini, Gland (CH); Cindy Trinh, San Marcos, CA (US); Dong Ik Shin, Poway, CA (US)

(73) Assignee: INNOVHEART S.r.l., Milan (IT)

( * ) Notice: Subject to any disclaimer, the term of this patent is extended or adjusted under 35 U.S.C. 154(b) by 0 days.

(21) Appl. No.: 16/522,164

(22) Filed: Jul. 25, 2019

(65) Prior Publication Data
US 2021/0022853 A1  Jan. 28, 2021

(51) Int. Cl.
*A61F 2/24* (2006.01)
*A61M 25/00* (2006.01)

(52) U.S. Cl.
CPC ............ *A61F 2/2412* (2013.01); *A61F 2/243* (2013.01); *A61F 2/2409* (2013.01); *A61F 2/2436* (2013.01); *A61M 25/0026* (2013.01); *A61F 2210/0014* (2013.01); *A61F 2220/0016* (2013.01); *A61M 2025/0024* (2013.01)

(58) Field of Classification Search
CPC .... A61F 2/2409; A61F 2/2412; A61F 2/2436; A61F 2/2439; A61F 2250/006; A61F 2220/0033; A61F 2220/0016; A61M 25/0026; A61M 2025/0024
See application file for complete search history.

(56) References Cited

U.S. PATENT DOCUMENTS

| 6,530,952 B2 * | 3/2003 | Vesely .................... A61F 2/243 623/2.18 |
| 7,736,388 B2 | 6/2010 | Goldfarb et al. |
| 10,470,884 B2 | 11/2019 | Bortlein et al. |
| 2002/0029079 A1 | 3/2002 | Kim et al. |
| 2002/0156526 A1 | 10/2002 | Hlavka et al. |

(Continued)

FOREIGN PATENT DOCUMENTS

| CN | 104244841 B | 12/2014 |
| EP | 2755562 B1 | 7/2014 |

(Continued)

OTHER PUBLICATIONS

Italian Search Report, issued from the Italian Patent Office in corresponding Italian Application No. 102019000015653, dated Jun. 3, 2020 (9 pages).

(Continued)

*Primary Examiner* — Katherine M Rodjom
(74) *Attorney, Agent, or Firm* — Flynn Thiel, P.C.

(57) ABSTRACT

A device for implanting a heart prosthesis including a central body, a containment portion having one or more sub-components, and a release device for the central body capable of being inserted into a catheter. A device for assisting the connection operation between the central body and the sub-components of the containment portion includes an assembly of catheters, of which there are at least two catheters for each sub-component of the containment portion, the catheters being joined to each other over a portion thereof and having at least one free end for each catheter.

12 Claims, 14 Drawing Sheets

(56) References Cited

U.S. PATENT DOCUMENTS

| | | |
|---|---|---|
| 2005/0222663 A1 | 10/2005 | Simpson et al. |
| 2005/0240147 A1 | 10/2005 | Makower et al. |
| 2008/0228265 A1 | 9/2008 | Spence et al. |
| 2008/0228267 A1* | 9/2008 | Spence ............... A61B 17/0487 623/2.36 |
| 2009/0254165 A1* | 10/2009 | Tabor ..................... A61F 2/844 623/1.11 |
| 2010/0331971 A1 | 12/2010 | Keränen et al. |
| 2011/0218620 A1* | 9/2011 | Meiri .................... A61F 2/2427 623/2.11 |
| 2012/0010700 A1 | 1/2012 | Spenser |
| 2013/0231735 A1 | 9/2013 | Deem et al. |
| 2015/0127093 A1 | 5/2015 | Hosmer et al. |
| 2015/0230919 A1 | 8/2015 | Chau et al. |
| 2015/0245910 A1 | 9/2015 | Righini et al. |
| 2015/0257881 A1* | 9/2015 | Bortlein ................ A61F 2/2418 623/2.11 |
| 2016/0256272 A1 | 9/2016 | Weber |
| 2016/0346080 A1 | 12/2016 | Righini et al. |
| 2017/0056176 A1 | 3/2017 | Rowe et al. |
| 2019/0167420 A1 | 6/2019 | Spence et al. |
| 2019/0192295 A1 | 6/2019 | Spence et al. |

FOREIGN PATENT DOCUMENTS

| | | |
|---|---|---|
| EP | 2755562 B8 | 7/2014 |
| EP | 2822473 B1 | 1/2015 |
| EP | 3158975 A1 | 4/2017 |

OTHER PUBLICATIONS

Italian Search Report, issued from the Italian Patent Office in related Italian Application No. 102019000015494 dated May 27, 2020 (10 pages).

Co-Pending U.S. Appl. No. 16/522,204, Applicant: Innovheart S.r.L., filed Jul. 25, 2019, Device for Arranging Guidewires Around a Heart Valve.

Danny Dvir, MD, "Transseptal Instead of Transapical Valve Implantation", JACC: Cardiovascular Interventions, vol. 9, No. 11, 2016, Elsevier, Vancouver, British Columbia, Canada (3 pages).

* cited by examiner

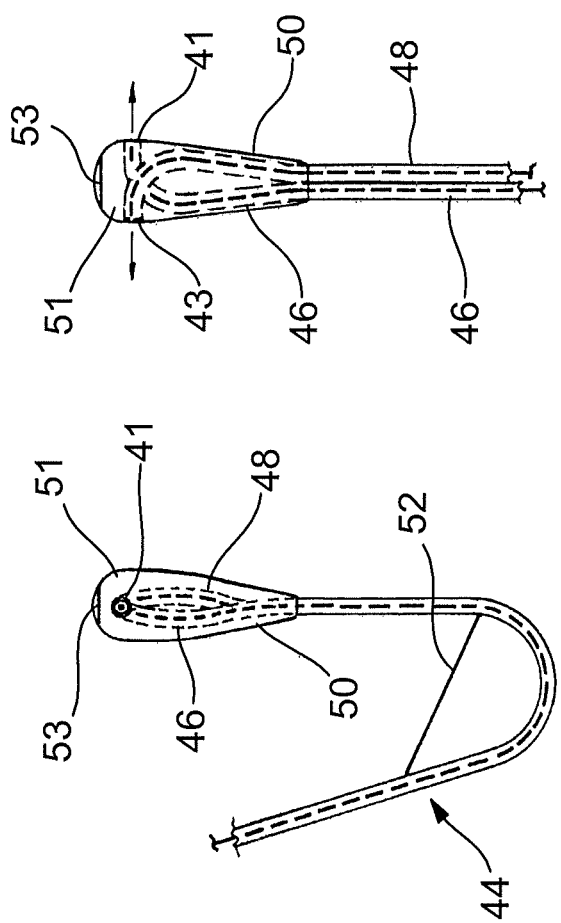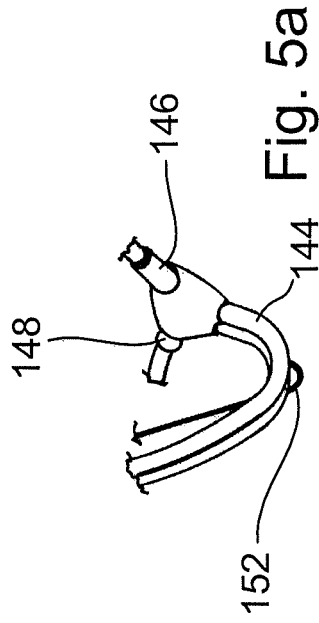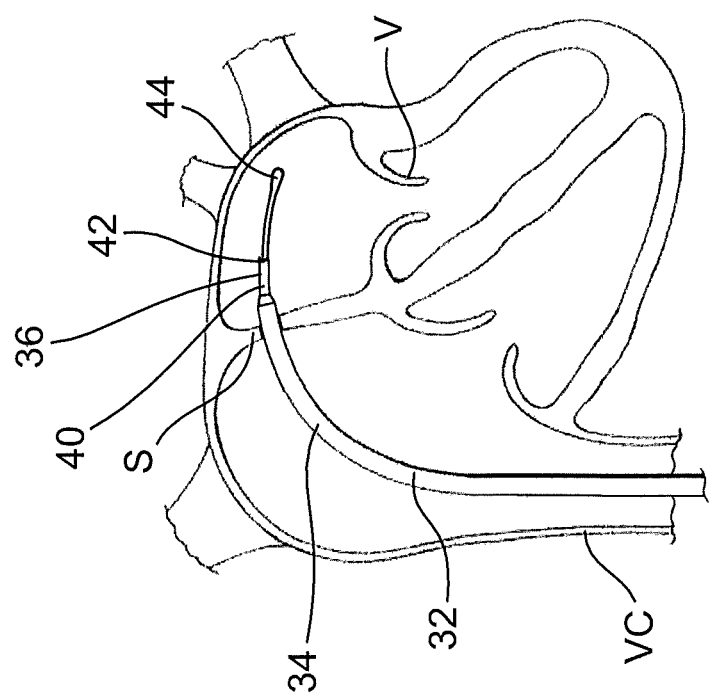
Fig. 5
Fig. 5a
Fig. 4
Fig. 3

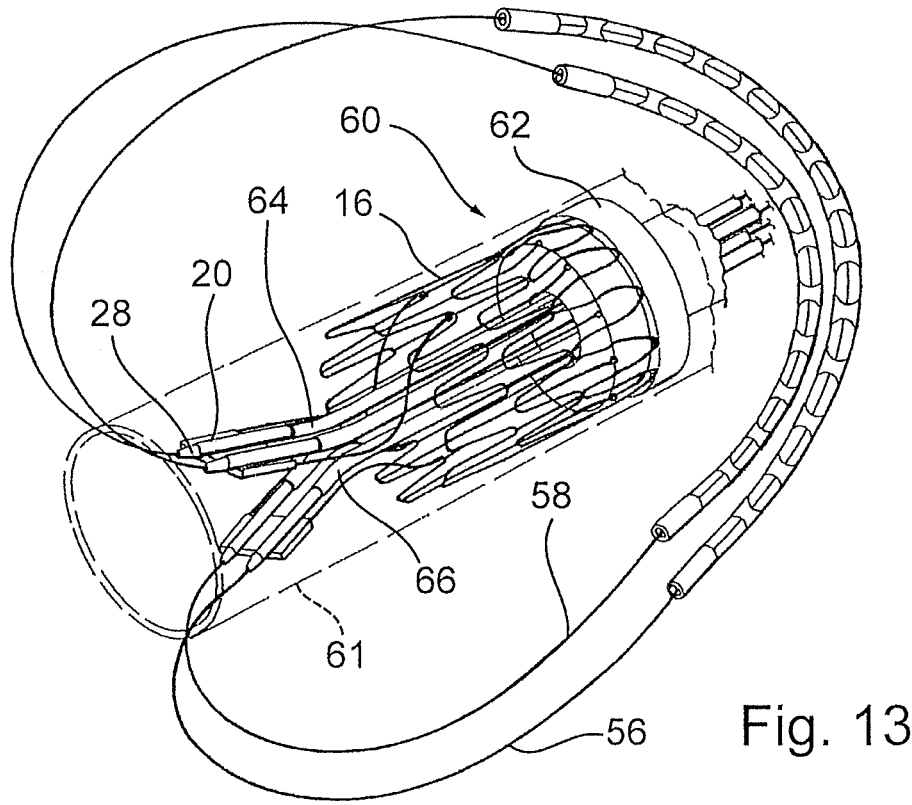
Fig. 13
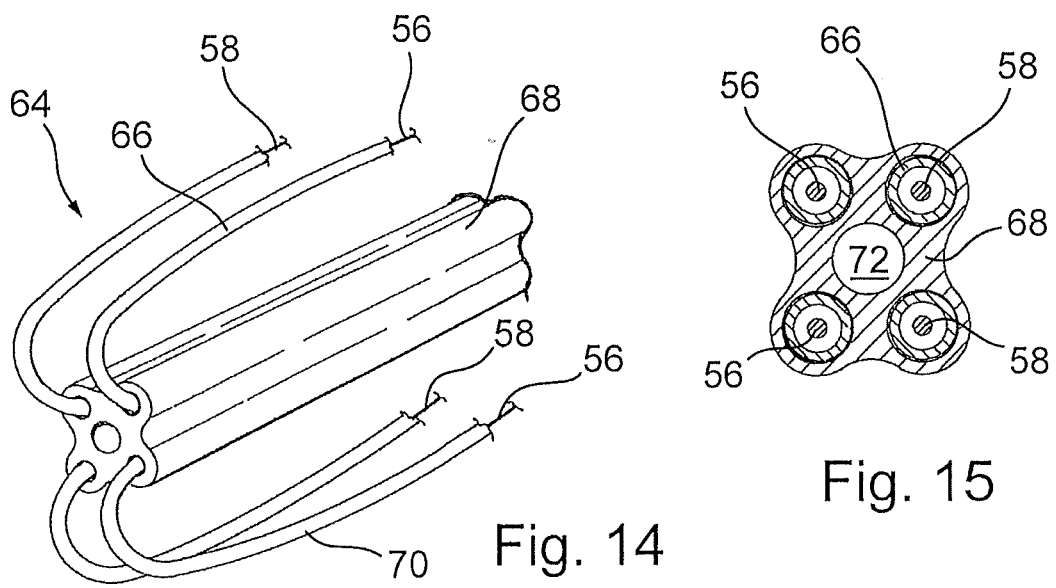
Fig. 14
Fig. 15

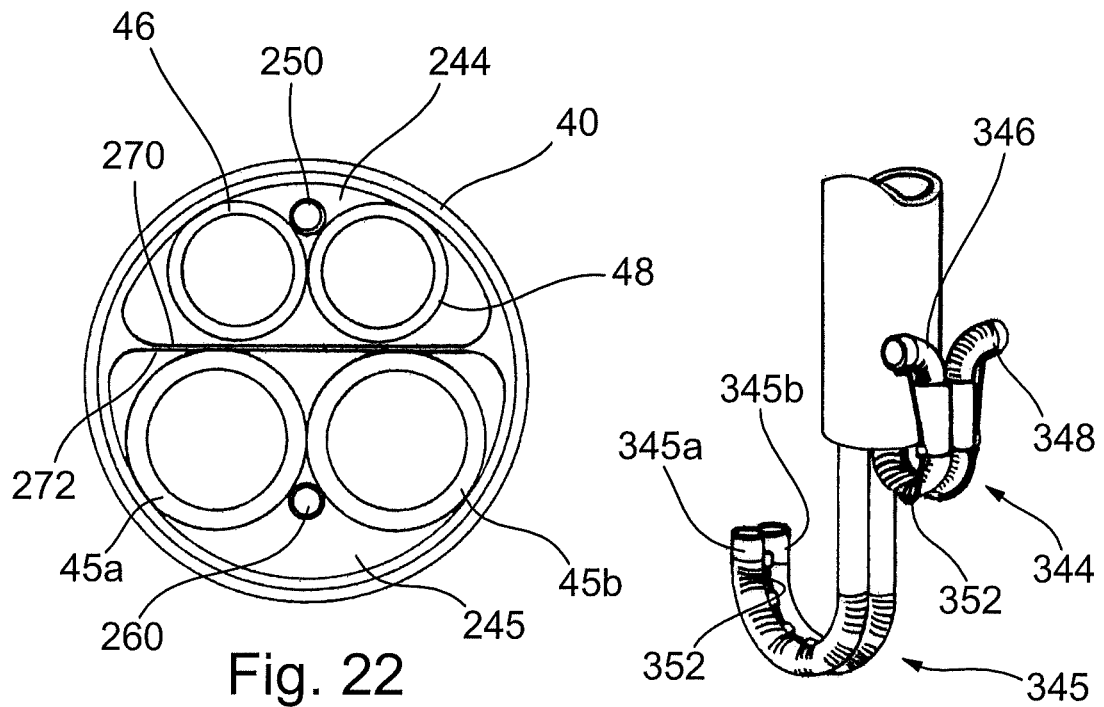
Fig. 22
Fig. 23
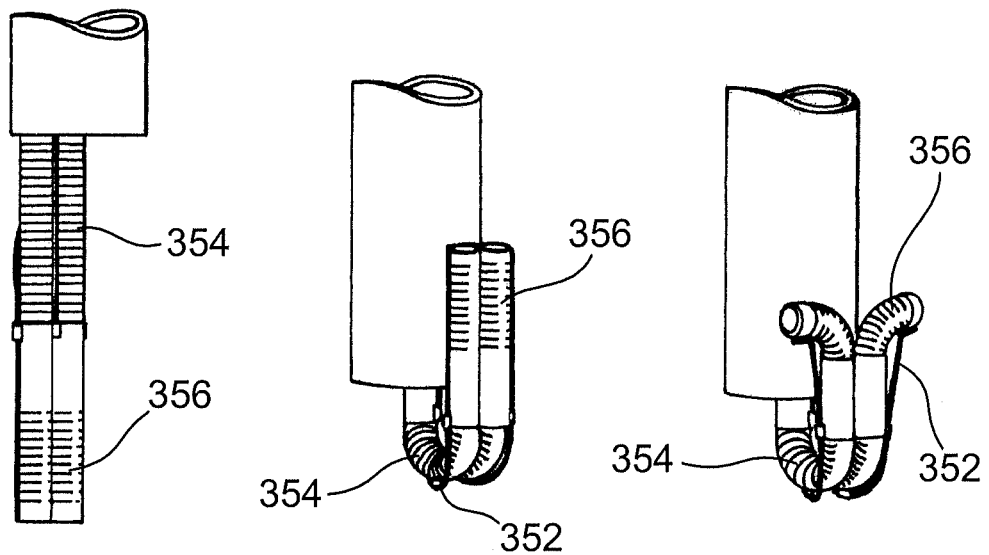
Fig. 24   Fig. 25   Fig. 26

DEVICE FOR IMPLANTING A PROSTHESIS FOR A HEART VALVE AND ASSEMBLY PROCEDURE

FIELD OF THE INVENTION

The present invention relates to a device for implanting a prosthesis for a heart valve and an assembly procedure.

The invention has been developed with particular regard, though in a non-limiting manner, for a device for use during a procedure for implanting a heart prosthesis for replacing the physiological function of a malfunctioning heart valve and in particular a heart prosthesis for an atrio-ventricular heart valve.

TECHNOLOGICAL BACKGROUND

Heart valves are complex and delicate organs which govern the correct function of the human heart. The main objective thereof is to make the blood flow inside the cardiac cavities unidirectional, being essential both in the filling phase of the cavity, the diastolic phase, and in the discharge phase of the blood, the systolic phase.

In order to optimize the efficiency of the pumping action of the blood, the heart is structured in two different compartments, right and left, respectively, each of which is in turn subdivided into two chambers, the atrium and ventricle, respectively. The right compartment of the heart, which is composed by the right atrium and ventricle, returns the blood from the peripheral circulation and directs it towards the pulmonary circulation for oxygenation thereof. The left compartment, which is similarly subdivided into left atrium and ventricle, supplies the peripheral vascularization, returning the oxygenated blood from pulmonary circulation and pumping it towards the systemic circulation.

In order to make the blood flow unidirectional inside the heart, a valve is positioned at the outlet of each chamber. The valves which are positioned at the outlet of the atria are the atrio-ventricular valves because they connect the atrial chamber to the ventricular chamber of each side of the heart. At the right side of the heart, this valve is also referred to as the tricuspid valve, at the left side it is usually indicated as the mitral valve. Finally, the valve which is positioned at the outlet from the right ventricle is called the pulmonary valve while the valve at the outlet from the left ventricle is called the aortic valve.

Pathologies which affect the function of a heart valve are among the most serious in the cardiovascular field. Among these, the insufficiency of the mitral valve, that is to say, the incapacity thereof to close completely, is a valve pathology which is highly impairing because it reduces the efficiency of the pumping action at the left side of the heart, which is responsible for blood circulation for the entire body.

In the current prior art, the standard therapy for treating severe valve malfunctions is the replacement of the valve with an implantable prosthesis. In other cases, mainly in the case of malfunctions of the mitral valve, there is provision for the repair thereof. In both cases, it is provided via an open-heart surgical procedure which affords direct access to the malfunctioning valve. This procedure requires the temporary arrest of the heart and the creation, by means of suitable pumps and oxygen exchangers, of an extracorporeal artificial blood circulation. Notwithstanding the refinement of the techniques for managing the cardiac arrest and improving the extracorporeal circulation systems, the therapy in open heart conditions presents risks as a result of the invasive nature thereof and the duration of the procedure.

In fact, the implantable prostheses, both for repairs and for replacements, commonly used during the conventional surgery usually require a long operation for fixing at the location of the implantation by means of specific suture techniques. In some cases, it is not even possible to intervene surgically as a result of the general conditions of the patient, for example, due to advanced age or the presence of concomitant pathologies.

In order to overcome these limitations, there have recently been developed procedures with interventions of reduced invasiveness, so-called transcatheter procedures. To this end, radially collapsible prostheses which can self-anchor at the implantation site are used. The prostheses can be implanted by means of catheters which are capable of navigating inside the vascular system and releasing the heart prosthesis by reaching the implantation site from a remote access created, for example, in a peripheral vessel, such as a femoral vein or artery. The valve malfunctions can thus be corrected with a beating heart and with limited use of surgical practices. In the current state, transcatheter techniques are clinical standard of care only for treating the aortic valve.

The situation is different with regard to the treatment of malfunctions of the atrio-ventricular valves, in particular the treatment of mitral insufficiency. The complex anatomical configuration of the valve and of the structures which surround it, the variability of the pathologies, also very different from each other, which affect the valve directly or indirectly, make it extremely difficult to comply with the requirements for a reliable and effective implantation in a mitral valve via the transcatheter route.

In the variety of single designs developed, the main technologies developed for transcatheter prostheses for atrio-ventricular valves provide for apical access to the heart. The procedure requires a thoracic incision in order to expose the apex of the left ventricle. Subsequently, the cardiac apex is punctured in order to be able to insert an apical port. Via the apical port, the catheters necessary to complete the procedure are inserted successively.

A problem of this approach is that it brings about damage to the heart in a rather delicate portion, such as the apex, with consequences that can be detrimental to the patient, such as bleeding, aneurisms, etc.

STATEMENT OF THE INVENTION

An object of the invention is to solve the problems of the prior art and in particular to provide a procedure for implanting a heart prosthesis which is transcatheter and which does not damage the apex of the heart. Another object is to provide a procedure which is even safer for the patient. In particular, an object is to provide a guidewire introducer device and a device for implanting a heart prosthesis which are reliable during use and safe in order to allow such a procedure to be carried out. Another object is to provide a procedure for assembling a heart prosthesis using such a device for implantation.

An embodiment relates to a guidewire introducer device and a device for implanting a heart prosthesis which are developed specifically for allowing a transcatheter implantation procedure with transseptal access. With transseptal access it is intended to be understood an access to the mitral valve which, starting from a peripheral femoral vein, navigates in the inferior vena cava up to the right atrium and finally arrives at the left atrium through an aperture which is created, with interventional methods, in the septum between the two atria. The left atrium affords anterograde access to the mitral valve to be treated. In this manner, damage, that is to say perforation, of the left ventricle which is associated with the transapical procedure, that provides access to the mitral valve from the ventricular side, that is to say retrograde, is prevented.

According to a first aspect, there is described herein a guidewire introducer device for positioning at least one guidewire around a heart valve. The device may be capable of deploying guidewires through transseptal access. The device may comprise a first catheter which may be provided with at least one distal deflection system. The device may comprise a second catheter which may be inserted inside the first catheter. The second catheter may comprise a lumen which is suitable for having a guidewire sliding therein. The second catheter may be provided with a distal deflection system for deflecting the end thereof, preferably through an angle greater than 90° in order to allow the zone immediately under the leaflets of the native valve to be best reached. The device may comprise a third catheter. The third catheter may be inserted inside the first catheter. The third catheter may have therein a device for capturing the guidwires. The third catheter may be provided with a distal deflection system. The deflection system of the second catheter may comprise a wire.

According to another aspect, there is described herein a guidewire introducer device for deploying at least two guidewires around a heart valve. The second catheter may comprise two lumens which are suitable for having guidewires sliding therein. The two lumens may terminate so as to face in substantially mutually opposite directions.

According to an advantageous aspect, a guidewire introducer device comprises a second catheter. The guidewire introducer device is provided with a radiopaque and/or echo-opaque element. The radiopaque/echo-opaque element may be positioned on a distal tip of the second catheter, preferably embedded therein.

According to another aspect, a guidewire introducer device may comprise a first catheter with a single lumen.

According to another aspect, there is described herein a procedure for positioning at least one guidewire around a heart valve; the procedure may comprise the step of providing access for a first catheter through a vein, preferably the femoral vein. The first catheter may be introduced inside the right atrium, through the inferior vena cava IVC. There may be produced a puncture in the septum between the two atria in order to access the left atrium. The procedure may comprise the step of inserting a guidewire introducer device in the left ventricle, passing though the mitral valve, and deploying one or more guidewires around the native valve.

According to a preferred aspect, there is described herein a procedure for positioning at least one guidewire around a heart valve, the procedure comprising the steps of:

providing access for a first catheter through a vein,
inserting the first catheter inside the right atrium, through the inferior vena cava and entering the left atrium through a puncture of the septum between the two atria,
inserting a guidewire introducer device into the left ventricle, passing through the mitral valve, and positioning one or more guidewires around the native valve.

According to another aspect, there is described herein a device for implanting a heart prosthesis. The heart prosthesis may comprise a central body and a containment portion. The containment portion may be subdivided into one or more sub-components. The device for implanting a heart prosthesis may comprise a release device for the central body. The release device may be capable of being inserted into a catheter. The device for implanting a heart prosthesis may comprise a device for assisting the connection operation between the central body and the sub-components of the containment portion. The device for assisting the connection operation between the central body and the sub-components of the containment portion may comprise an assembly of catheters. There may be at least two catheters for each sub-component of the containment portion. The catheters may be joined to each other via a portion thereof and may each have at least one free end. The catheters may be grouped together in the same sheath. The sheath may group together the catheters along a portion thereof. The sheath may leave free at least one end for each catheter. The sheath may further comprise an additional lumen for a guidewire, preferably a central one. Advantageously, the catheters which constitute the assembly of catheters may be steadily joined to each other.

According to another aspect, a device for assisting the connection operation between the central body and the sub-components of the containment portion may comprise an assembly of catheters which are incompressible in a longitudinal direction. In this manner, during use, they form an incompressible abutment channel for a guidewire. Preferably, the catheters which constitute the assembly of catheters may be flexible.

According to another aspect, there is described herein a procedure for assembling a heart prosthesis. The heart prosthesis may comprise a central body and a containment portion. The containment portion may be subdivided into one or more sub-components. The procedure described may comprise the step of inserting a guidewire into each sub-component of the containment portion. It may comprise the step of sliding the sub-components in such a manner that both the ends of the guidewire are outside the sub-component itself. The procedure may comprise the step of inserting, for each sub-component of the containment portion, each end of the guidewire in a corresponding connecting element, for the connection of the central body and the containment portion. The procedure may comprise the step of inserting each end of the guidewire into a corresponding catheter of the assembly of catheters. It may comprise the step of drawing the ends of each guidewire in order to connect the central body and the sub-components of the containment portion.

According to another aspect, there is also described herein a procedure for implanting a heart prosthesis. The heart prosthesis may comprise a central body and a containment portion, which is sub-divided into one or more sub-components. The procedure may comprise the step of affording access for a first catheter through a vein. Preferably, the access may be afforded in the femoral vein. The procedure may comprise the step of inserting the first catheter through the inferior vena cava IVC. The first catheter may be inserted up to inside the right atrium. There may be created a puncture in the septum between the two atria. Through this puncture, it is possible to access the left atrium. The procedure may comprise the step of providing one or more guidewires around the native valve; this operation may be carried out by means of a guidewire introducer device. It is possible to insert the sub-components of the containment portion. The procedure may comprise the step of inserting a device for implanting a heart prosthesis. It is then possible to connect the central body to the sub-components 22 of the containment portion 18. The release in position of the central body may be brought about by pushing the central body out of the device for implantation.

According to another aspect, the procedure for implanting a heart prosthesis provides for the step of inserting each sub-component into the heart by guiding it with at least one guidewire which is arranged around the native valve, preferably sliding each sub-component over the at least one guidewire (over the wire).

According to another aspect, the procedure for implanting a heart prosthesis may provide for using a device for implanting a heart prosthesis comprising a device for assisting the operation of connecting the central body and the sub-components of the containment portion which may comprise an assembly of catheters; the procedure may comprise the steps of inserting each end of the guidewire into a corresponding connecting element for the connection of the central body and the containment portion and inserting each end of the guidewire into a corresponding catheter of the assembly of catheters, in the free end thereof. The procedure may further comprise the step of acting on the ends of the guidewire in order to establish the connection between the central body and the sub-component of the containment portion.

According to another aspect, there is described herein a procedure for implanting a heart prosthesis comprising a central body for prosthetic leaflets and a containment portion which is subdivided into one or more sub-components, the procedure comprising the steps of:
  providing access for a first catheter through a vein,
  inserting the first catheter inside the right atrium, though the inferior vena cava and accessing the left atrium through a puncture of the septum,
  providing one or more guidewires around the native valve,
  inserting the sub-components of the containment portion,
  inserting a device for implantation of a heart prosthesis,
  connecting the central body to the sub-components of the containment portion, and
  pushing the central body until it is caused to be released in position.

There is further described herein a procedure for implanting a heart prosthesis, in which each sub-component is inserted by sliding it over one of the guidewires which are arranged around the native valve.

Advantageously, a procedure for implanting a heart prosthesis uses a device for implanting a heart prosthesis with all or some of the above-described features; according to the procedure, after inserting the sub-components, for each sub-component of the containment portion there are carried out the steps of:
  inserting each end of the guidewire into a corresponding connecting element, for the connection of the central body and the containment portion,
  inserting each end of the guidewire in a corresponding catheter of the assembly of catheters, at the free end thereof, and
  tensioning the ends of the guidewire, bringing about the connection between the central body and the sub-component of the containment portion. Preferably, the access is brought about by means of a femoral vein.

BRIEF DESCRIPTION OF THE DRAWINGS

The solution according to one or more embodiments of the invention, as well as additional characteristics and the relative advantages, will be better understood with reference to the following detailed description which is given purely by way of non-limiting example and which is intended to be read with the appended Figures, in which for simplicity corresponding elements are referred to with identical or similar reference numerals and the explanation thereof is not repeated. In this regard, it may be expressly understood that the Figures are not necessarily to scale, with some details which may be exaggerated and/or simplified and that, unless indicated otherwise, they are simply used to conceptually illustrate the structures and the procedures described.

In particular:

FIG. 3 shows a step of the procedure for implanting the heart prosthesis, in which access is afforded by means of the interatrial septum.

FIG. 4 shows a detail of the second catheter of the guidewire introducer device.

FIG. 5 is a different view of the same detail as FIG. 4.

FIG. 5a shows a variant of the second catheter of the guidewire introducer device.

FIG. 13 shows a step of the procedure for implanting the heart prosthesis, in which a device for implanting a heart prosthesis is inserted.

FIG. 14 is a view of a device for assisting the connection operation between the central body and the sub-components of the containment portion.

FIG. 15 is a cross-section of the device of FIG. 14.

FIG. 22 is a cross-section of a variant of the second and third catheters of the guidewire introducer device.

FIGS. 23 to 26 show another variant of the second and third catheters of the guidewire introducer device.

DETAILED DESCRIPTION

Figure 1:
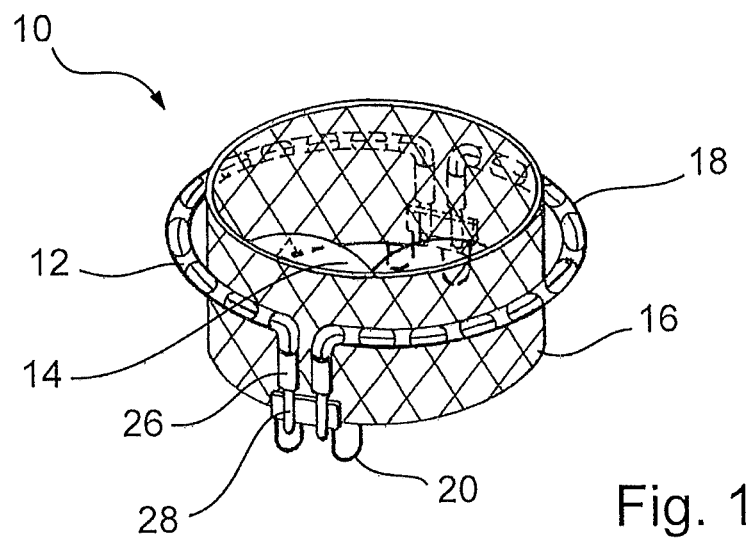
FIG. 1 is a general schematic illustration of a heart prosthesis for treating heart valves, in accordance with an embodiment of the invention.
Figure 2:
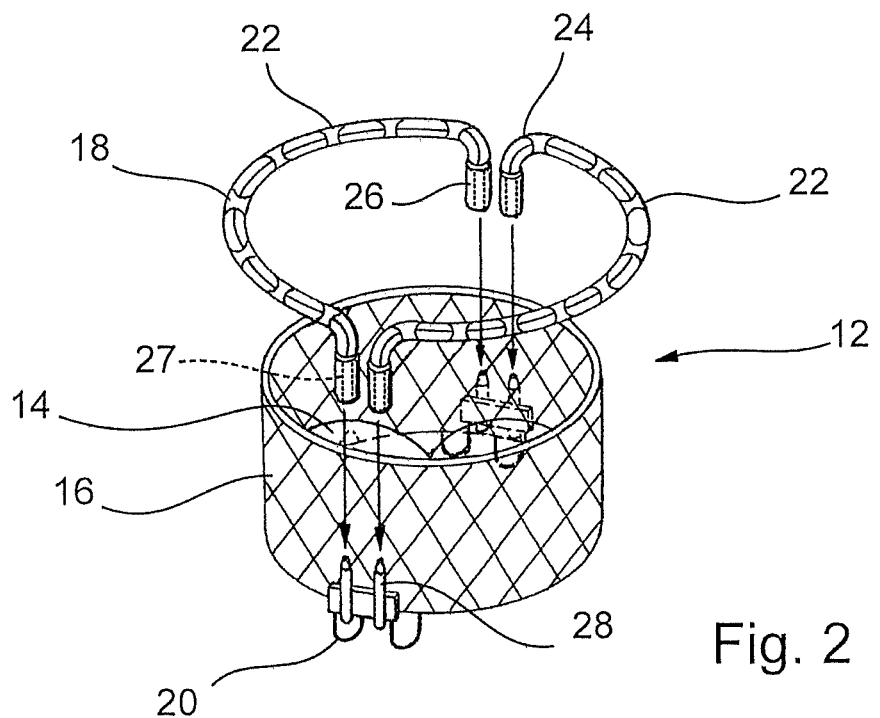
FIG. 2 shows the heart prosthesis of FIG. 1 in a disassembled state.

Now with reference to the drawings, in FIGS. 1 and 2 there is described an implantable heart prosthesis 10 which is used to replace the functionality of an atrio-ventricular valve.

The heart prosthesis 10 comprises a prosthetic structure 12 for support and interfacing with the native valve and by a group of flexible prosthetic leaflets 14 which are fixed therein. The prosthetic structure 12 comprises in particular:
- a central body 16,
- a containment portion 18, and
- connecting elements 20 for connecting the central body 16 and the containment portion 18.

The prosthetic structure 12, as for each of the elements thereof, is configured so as to be collapsible without any consequence for the safety and the functionality of the heart prosthesis. Therefore, it is possible to temporarily reduce the radial dimensions of the prosthesis in order to allow the introduction thereof inside the cardiac cavities through access ports which have a reduced aperture and which are compatible with the techniques of minimal invasive surgery, and in particular with the techniques of transcatheter positioning and heart prosthesis implantation according to the present invention. In other words, it is possible to insert the heart prosthesis 10 inside a catheter with a small radial profile, which is capable of conveying the prosthesis inside the heart cavity, near the implantation site, through a minimal invasive access, and there to carry out the deployment and the implantation thereof, functionally replacing the native valve.

There are described in detail herein below the different portions into which the prosthetic structure 12 is divided.

The central body 16 is the portion of the prosthetic structure 12 which delimits the conduit for the passage of blood through the device. There are fixed inside the central body 16 the flexible prosthetic leaflets 14 which make the blood flow unidirectional inside the conduit, as known, for example, from the Italian patent No. 0001422040 by the same Applicant.

The central body 16 is a radially collapsible resilient structure which tends, as a result of resilient return, also to expand to a diameter greater than the maximum diameter which maintains coaptation, that is to say, the contact, between the free edges of the closed prosthetic leaflets 14.

The containment portion 18 is the portion of the prosthetic structure which counteracts and limits the free expansion of the central body 16, preventing it from exceeding the maximum diameter which is compatible with the preservation of coaptation between the prosthetic leaflets 14. The containment portion 18 has a substantially annular geometry and is longitudinally inextensible, that is to say, it does not modify significantly the peripheral extent thereof even when the central body 16 expands inside it while applying a radial force outward.

The containment portion 18 is preferably subdivided into two sub-components 22 which are separated from each other, substantially in the form of an arc; for simplicity, the two sub-components will be indicated below by the term "arcs". Each arc 22 can be selectively engaged with the connecting elements 20, with which it is steadily joined in the final implantation configuration.

Each end 24 of each sub-component 22 is equipped with an engagement portion 26, preferably capable of assuming orientations outside the annular plane. In the embodiment depicted, the engagement portion 26 is orientated substantially perpendicularly to the plane of the annulus. In turn, the connecting elements 20 are equipped with pins 28 which are suitable for being received in axial holes 27 which are present in the engagement portions 26. A pair of pins 28 is present on each of the two connecting elements 20, arranged substantially in angular positions which are diametrically opposed with respect to the central body 16. These pins 28, as well as the engagement portions 26 which are present at the ends of the arcs 22 of the containment portion 18, can be provided with barbs or lips or other surface discontinuities which are intended to create mechanical interference between the portions and/or to increase the friction in the pin/hole connection, improving the stability of the connection between the sub-components 22 of the containment portion 18 and the connecting elements 20. The pins 28 are orientated in a coherent manner relative to the orientation of the engagement portions 26 which are present on the sub-components 22 of the containment portion 18, so that the pin/hole connection maintains the containment portion in a geometrically consistent plane with the annulus of the native valve. Furthermore, the pins 28 are pierced axially in order to allow the passage of a guidewire, as better described below.

It is evident that the pin/hole connection mechanism could instead comprise a pin at the end of the sub-components 22 and a cylindrical hole in the connecting elements 20. More generally, the pin/hole connection has a purely exemplary purpose, without any limiting intention of the generality of the solution.

Naturally, the prosthesis may also comprise a different number of sub-components 22. For example, it may comprise a single sub-component and therefore be formed in the manner of an open ring. The version described with two sub-components 22 is the preferred one, however, because it allows the use of two guidewires which, as a result of the introducing device for guidewires described below, are easier to position correctly than a single guidewire which could remain entangled in the chordae tendineae. However, a third sub-component does not simplify the positioning operations and therefore is substantially unnecessary, but should not be excluded.

In use, the leaflets of the native valve remain entrapped inside the coupling between the central body 16 and the containment portion 18. Furthermore, the containment portion 18 also has the function of stabilizing the native valve annulus, preventing the radial force applied by the central body 16, while being necessary to ensure effective anchoring of the prosthesis, from being transferred to the surrounding anatomical structure which is usually affected by degenerative and dilating processes which are associated with the pathology which makes the atrio-ventricular valve malfunction.

For clarity reasons, in the drawings of FIGS. 1 and 2, as for in the Figures which follow, the external diameter of the central body 16 is illustrated having dimensions less than the internal dimensions of the containment portion 18. In other words, the Figures show these two components of the prosthetic structure 12 not in contact with each other in the configuration of full expansion. In reality, it is possible to have over-dimensioning of the central body 16 with respect to the dimensions of the containment portion 18. In this case, there is an interference between the two portions of the prosthetic structure 12 and effectively the central body 16 applies a radial pressure to the containment portion 18 when the latter carries out its constraining action with respect to the expansion, independently of the thickness of the tissue which remains captured in between the two portions of the prosthetic structure 12. This radial pressure increases the stability of the anchorage to the native valve leaflets.

There will now be described a preferred procedure for implantation of the heart prosthesis 10 described above.

Initially, there is afforded access through the femoral vein or the iliac vein. Where possible, the access from the femoral vein is preferred because it is significantly simpler and more direct. In particular, it doesn't require an invasive surgical procedure. An introducer catheter may be used with the main objective of protecting the femoral vein which has a small calibre.

The introducer catheter, when present, is positioned through the femoral vein in order to create the access to a vessel having a larger diameter. There is then inserted a main catheter 32 which slides inside the introducer catheter, when provided, through the inferior vena cava IVC up to the right atrium, as can be seen in FIG. 3.

The main catheter 32 is provided with a distal deflection system so that the end 34 thereof can be bent by the operator in the direction of the left atrium. A puncture in the septum S between the two atria is then performed, allowing access to the left atrium. Inside the main catheter 32, a guidewire introducer device 36 is inserted.

As mentioned above, it is not mandatory to provide an introducer catheter but instead there may be used directly a main catheter 32 which gains access to the right atrium through the inferior vena cava. Furthermore, the main catheter may also be inserted up to a location inside the left atrium; it thereby allows the insertion of the guidewire introducer device 36 directly in the left atrium.

The guidewire introducer device 36 is a device the function of which is to allow the deployment around the leaflets of the native mitral valve V of guidewires which are necessary for the subsequent positioning of the heart prosthesis 10.

The guidewire introducer device 36 comprises a first catheter 40, inside which a second catheter 44 and a third catheter 45 slide. The first catheter 40 is a single-lumen catheter. It is provided with a distal deflection system so that the end 42 thereof can be orientated by the operator in the direction of the mitral valve V.

The second catheter 44, which can better be seen in the detailed FIGS. 4 and 5, comprises two lumens 46 and 48 which are suitable for having guidewires sliding therein. The two lumens are arranged parallel with each other and beside each other over a greater portion of the second catheter 44. In the end 50 of the second catheter 44, the two lumens curve through an angle of approximately 90° in substantially opposite directions. The two lumens 46 and 48 therefore terminate not at a distal tip 51 of the catheter 44, but instead at the side thereof in diametrically opposed positions in respective holes 41 and 43. In other words, two guidewires inserted in the lumens 46 and 48 exit from the second catheter 44 oriented in diametrically opposed directions.

The second catheter 44 further comprises a deflection system. The deflection system according to the exemplary embodiment depicted comprises a wire 52. The wire 52 is fixed to the end 50 of the catheter, runs externally from the catheter over a short portion and then inside the catheter. The operator may pull the wire 52 in order to establish a curvature, which can be very pronounced, for the second catheter 44, as can clearly be seen in FIG. 4. The curvature is greater than 90°. However, it is not impossible to use other deflection systems. For example, inside the second catheter there may be incorporated a segment of a shape-memory material so that it can be inserted in a stretched state in the first catheter 40 and recovers the correct curvature when it is pushed out of the first catheter 40. An example of such a configuration is shown in FIG. 5a, in which a wire 152 of shape-memory material, for example, of titanium nickel alloy (Nitinol) is incorporated inside the second catheter 144.

There is provided at the distal tip 51 a segment 53 of radiopaque or echo-opaque material. The segment 53 is embedded inside the distal tip 51 which is preferably rounded in order to prevent accidental lesions.

The third catheter 45, as better described below, is also inserted inside the first catheter 40 and receives therein a guidewire capturing device 47 (a snaring device), as better described below. It may be noted that the guidewire capturing device which is depicted, comprising different collapsible rings or loops grouped together, is one of the many possible capturing devices which can be used that has been found to be particularly effective for the specific application. However, different capturing devices are not excluded, for example, having a single loop or a different number from the one of the device depicted.

Figure 6:
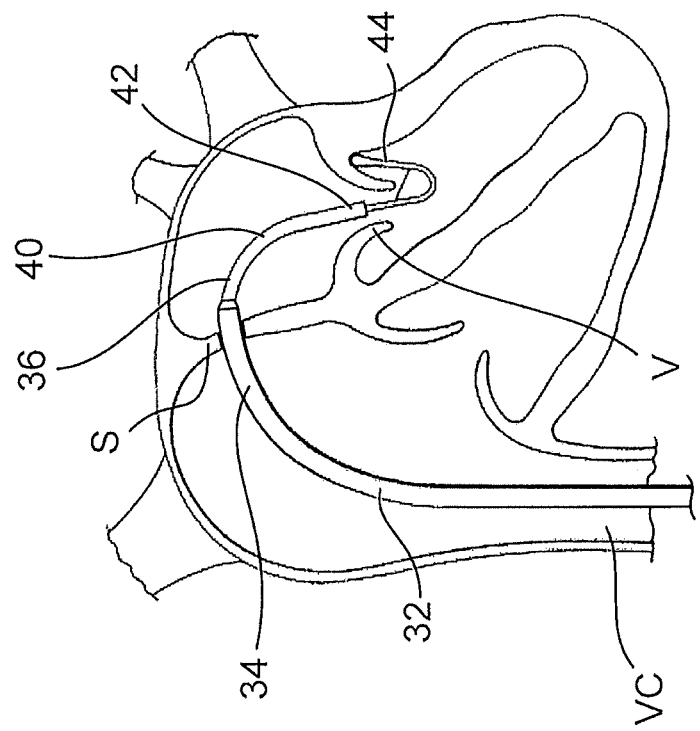
FIG. 6 shows a step of the procedure for implanting the heart prosthesis, in which the second catheter of the guidewire introducer device is caused to advance in the direction of the mitral valve.

Now turning to the procedure for implanting the heart prosthesis, the guidewire introducer device 36 which has been inserted inside the main catheter 32 is advanced inside the left atrium (FIG. 3), through the septum S. It may be noted that the end 34 of the main catheter 32 may be located in the right atrium, as in the Figure, or in the left atrium. The end 42 of the first catheter 40 of the guidewire introducer device 36 is bent so that it points towards the valve V, therefore towards the bottom in FIG. 6.

The second catheter 44 of the guidewire introducer device 36 is made to slide inside the first catheter 40 of the guidewire introducer device 36 (FIG. 6); the end 50 exits and takes on a pronounced curvature which is directed in the opposite direction to the curvature of the end 42 of the first catheter 40. The second catheter 44 is in fact bent upwards in FIG. 6.

Figure 7:
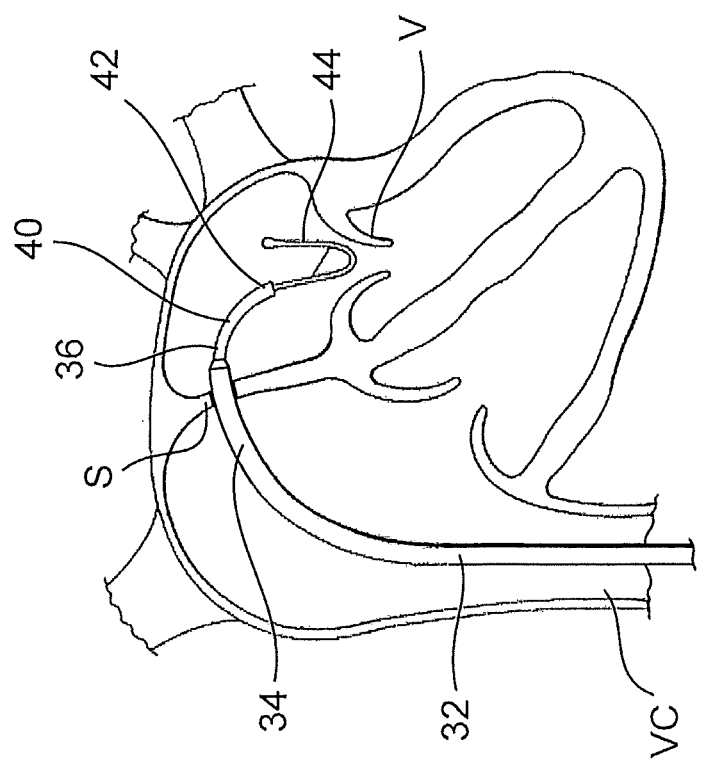
FIG. 7 shows a step of the procedure for implanting the heart prosthesis, in which the second catheter of the guidewire introducer device is caused to advance in the left ventricle through the mitral valve.

The guidewire introducer device 36 is advanced further (FIG. 7) inside the main catheter 32 and the second catheter 44 is pushed into the left ventricle, through the valve V.

Once the second catheter 44 of the guidewire introducer device 36 is inside the left ventricle, it is slightly retracted so that the distal tip 51 thereof is positioned behind the posterior leaflet of the native valve. In particular, the distal tip 51 is preferably positioned behind the central segment (scallop) which is normally designated as P2. To this end, the presence of the segment 53 of radiopaque material at the distal tip 51 is particularly advantageous. In case of doubts concerning the exact positioning or the orientation of the end 50 of the catheter, it is in fact possible to verify it directly with an ultrasound probe or by means of fluoroscopy. The segment 53 of radiopaque material is to be oriented in a direction tangent to the edge of the valve.

Figure 8:
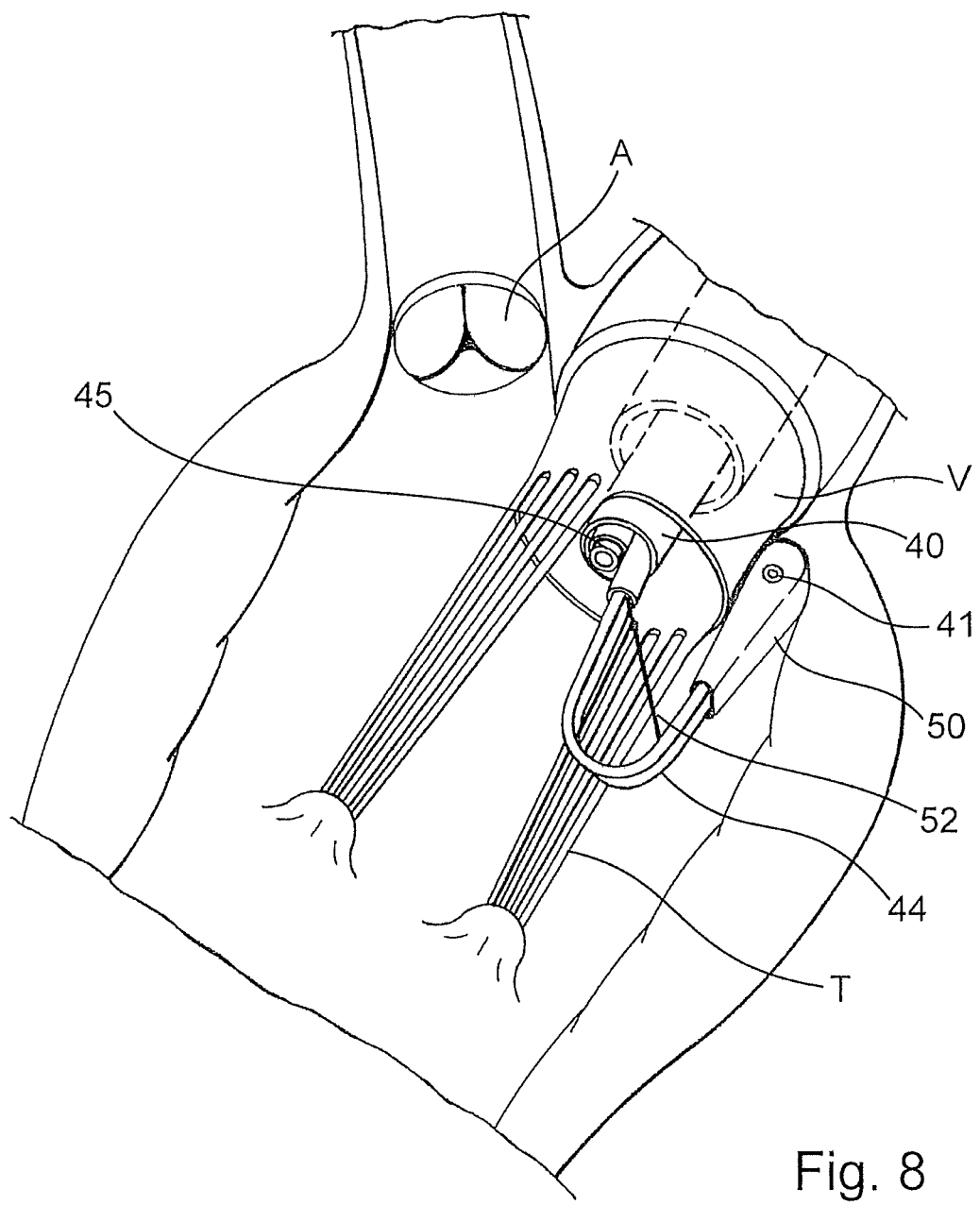
FIG. 8 shows the step of FIG. 7 in a close-up view.

FIG. 8 shows a detailed schematic view of the left ventricle, in which the native mitral valve V is clearly visible, with the two bundles of chordae tendineae T, as well as the aortic valve A. The end 50 of the second catheter 44 of the guidewire introducer device 36 is depicted in the correctly positioned state behind the posterior leaflet of the native valve V. It may be noted that the catheter 44 does not cross the bundles of chordae tendineae.

Figure 9:
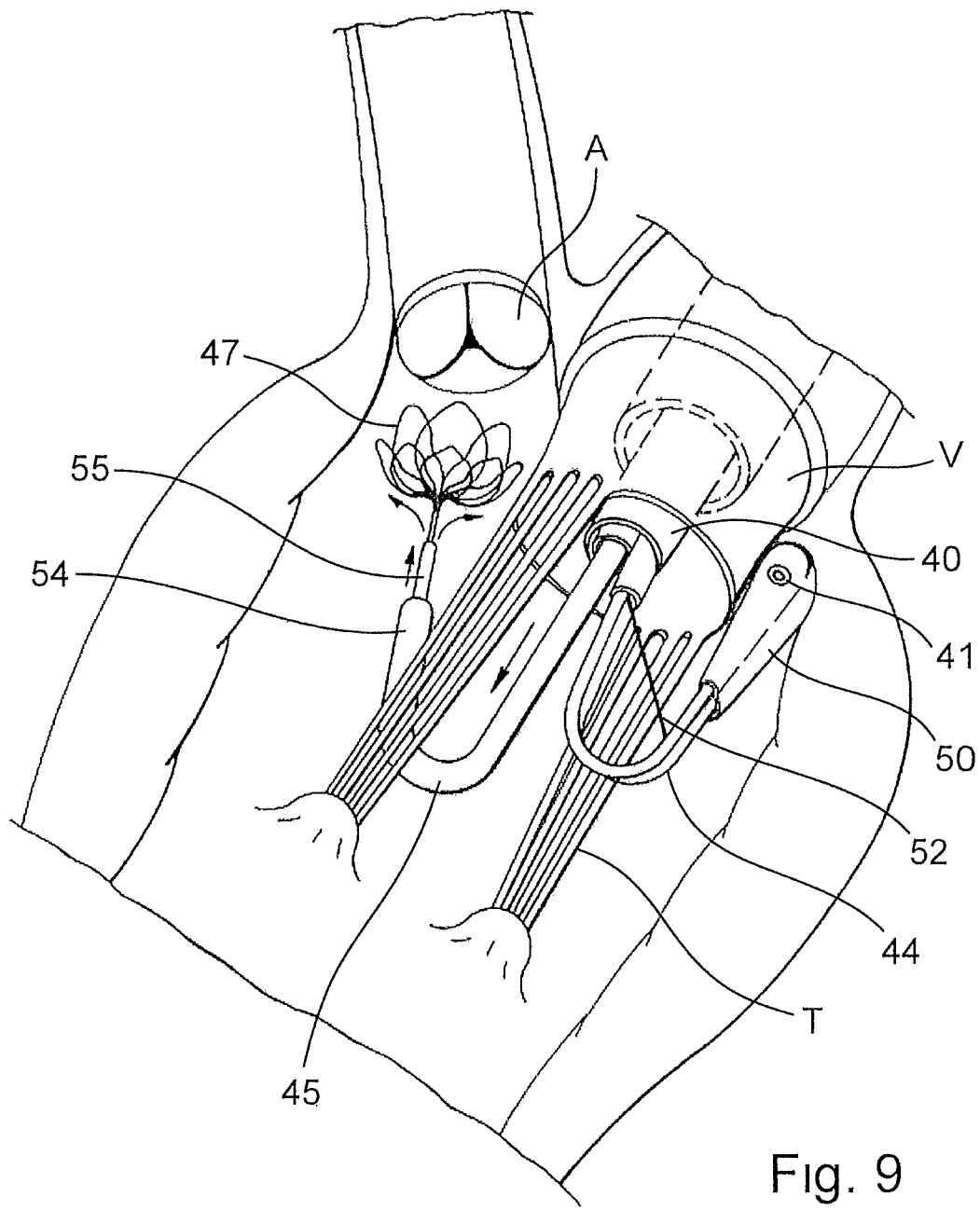
FIG. 9 shows a step of the procedure for implanting the heart prosthesis, in which a capture device for guidewires is positioned.

Now with reference to FIG. 9, the third catheter 45, with the guidewire capturing device 47 therein, is slided inside the first catheter 40 until it is introduced inside the left ventricle. The second catheter also has, near the end 54 thereof, a deflection system 56. This deflection system may be generally identical to the wire 52 described above with reference to the second catheter 44. According to a preferred variant, however, it is made for constructional simplicity with a wire which slides inside the wall of the catheter; a flexible metal structure with a rigid backbone embedded in the thickness of the catheter produces the effect of the curvature. Other known mechanisms in the prior art should not be excluded, however. Furthermore, the guidewire capturing device 47 is inserted in a covering sheath 55.

The third catheter 45 is orientated with the end 54 curved in an opposite direction with respect to the direction in which the end 50 of the second catheter is curved, therefore in the direction of the aortic valve. The guidewire capturing device 47 is pushed out of the respective third catheter 45 and out of the sheath 55 until it is positioned in the LVOT (left ventricular outflow tract), that is to say in front of the aortic valve.

Figure 10:
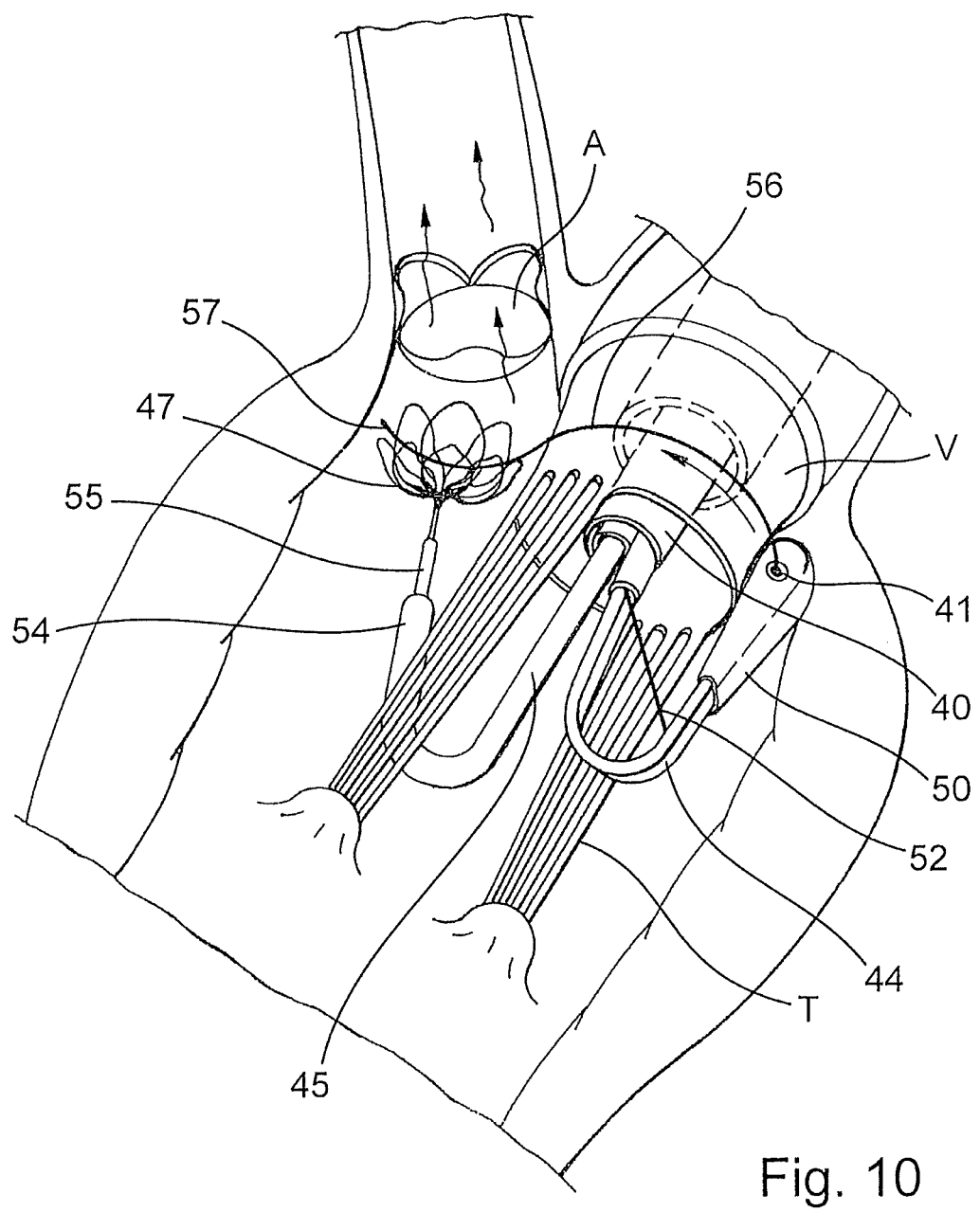
FIG. 10 shows a step of the procedure for implanting the heart prosthesis, in which a first guidewire is positioned.

By maintaining the guidewire capturing device 47 in this position, a first guidewire 56 is inserted in the first lumen 46 of the second catheter of the guidewire introducer device 36. The end 57 of the guidewire 56 is pushed (FIG. 10) into the ventricle by the operator. As a result of the effect of the precise positioning of the distal tip 51 of the second catheter 44, of the lateral position of the outlet 41 of the lumen 46, of the heart configuration, and of the blood stream that during systole is naturally directed towards the aortic valve A, the end 57 of the guidewire 56 is driven around the valve and in the direction of the LVOT. Once the LVOT has been reached, it is captured by the guidewire capturing device 47 which has already been positioned beforehand. Subsequently, the retrieval of the end 57 of the guidewire 56 is carried out, by withdrawing the third catheter 45.

Alternatively, it is also possible to position the guidewire capturing device 47 inside the aorta, that is to say beyond the aortic valve A. The guidewire will be pushed into the aorta by the blood flow and the capture operation may therefore be carried out.

Figure 11:
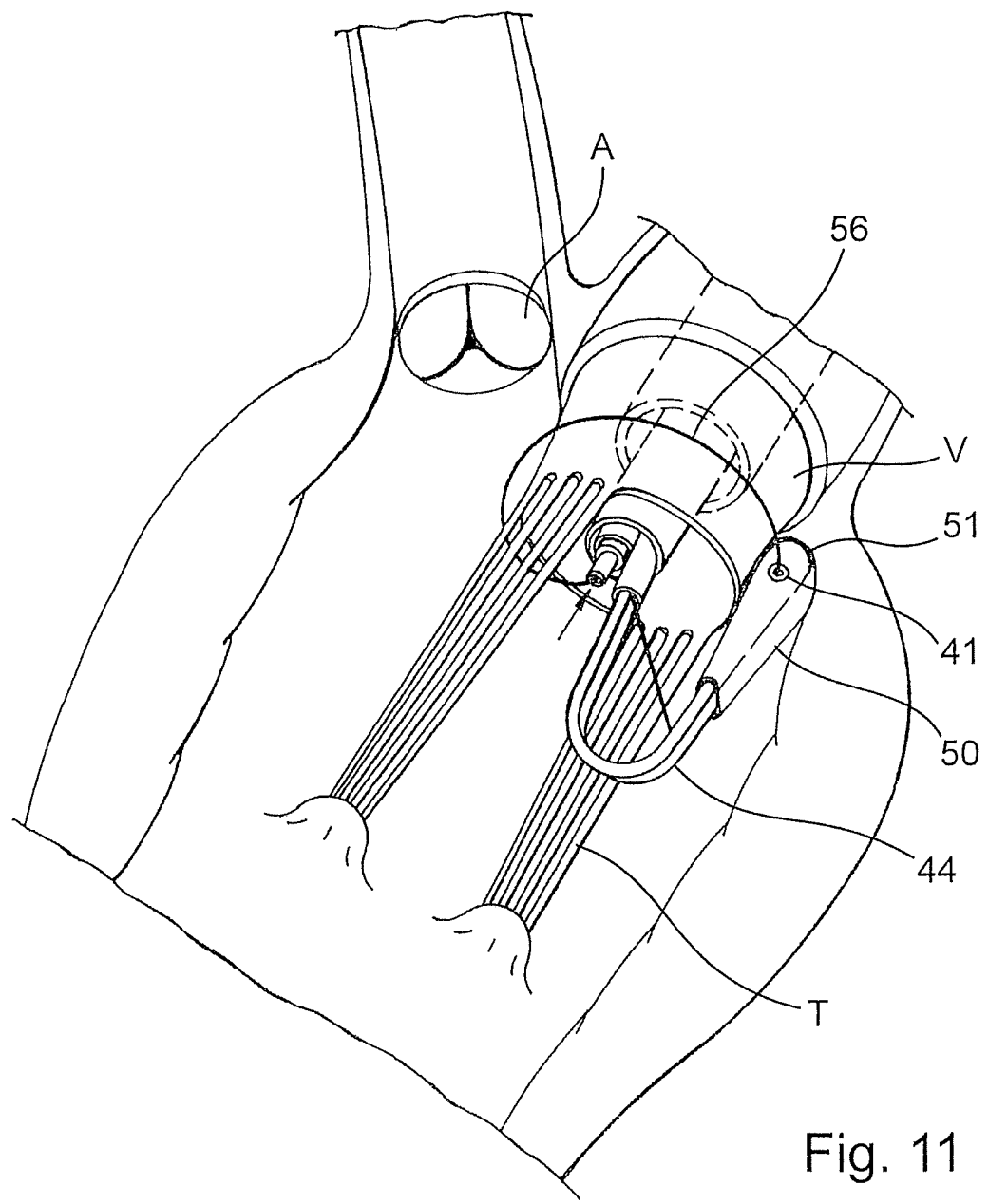
FIG. 11 shows a step of the procedure for implanting the heart prosthesis, in which the positioning of the first guidewire is completed.

Once the end 57 of the guidewire 56 has been captured, the guidewire 56 forms a half-loop around the valve V (FIG. 11).

In a generally symmetrical manner, it is carried out the formation of a similar half-loop around the valve V with a second guidewire 58 that is inserted into the second lumen 48 of the second catheter 44. In this manner, the valve V is completely surrounded by the two guidewires 56 and 58, which are correctly positioned. To this end, it is possible to use the same guidewire capturing device 47 which is used to capture the first wire or, preferably, another guidewire capturing device 47 which is also received in the third catheter 45. In this case, the third catheter 45 preferably has a double lumen.

Naturally, it is also possible to use a guidewire positioning device which is similar to the one described above in detail in order to position a single guidewire which carries out the complete loop around the native valve. In this case, however, the guidewire positioning procedure becomes more complex: although there are fewer steps necessary (it is not necessary to repeat the steps for the second wire), it is not easy to orientate a guidewire in a sufficiently precise manner around the entire valve because there is the risk of remaining entangled in the chordae tendineae. Indeed, using two guidewires allows to leverage the geometry of the heart and the natural blood flow to facilitate the operations and to minimize the risk of errors which can have serious consequences for the patient if not identified and corrected immediately.

Figure 12:
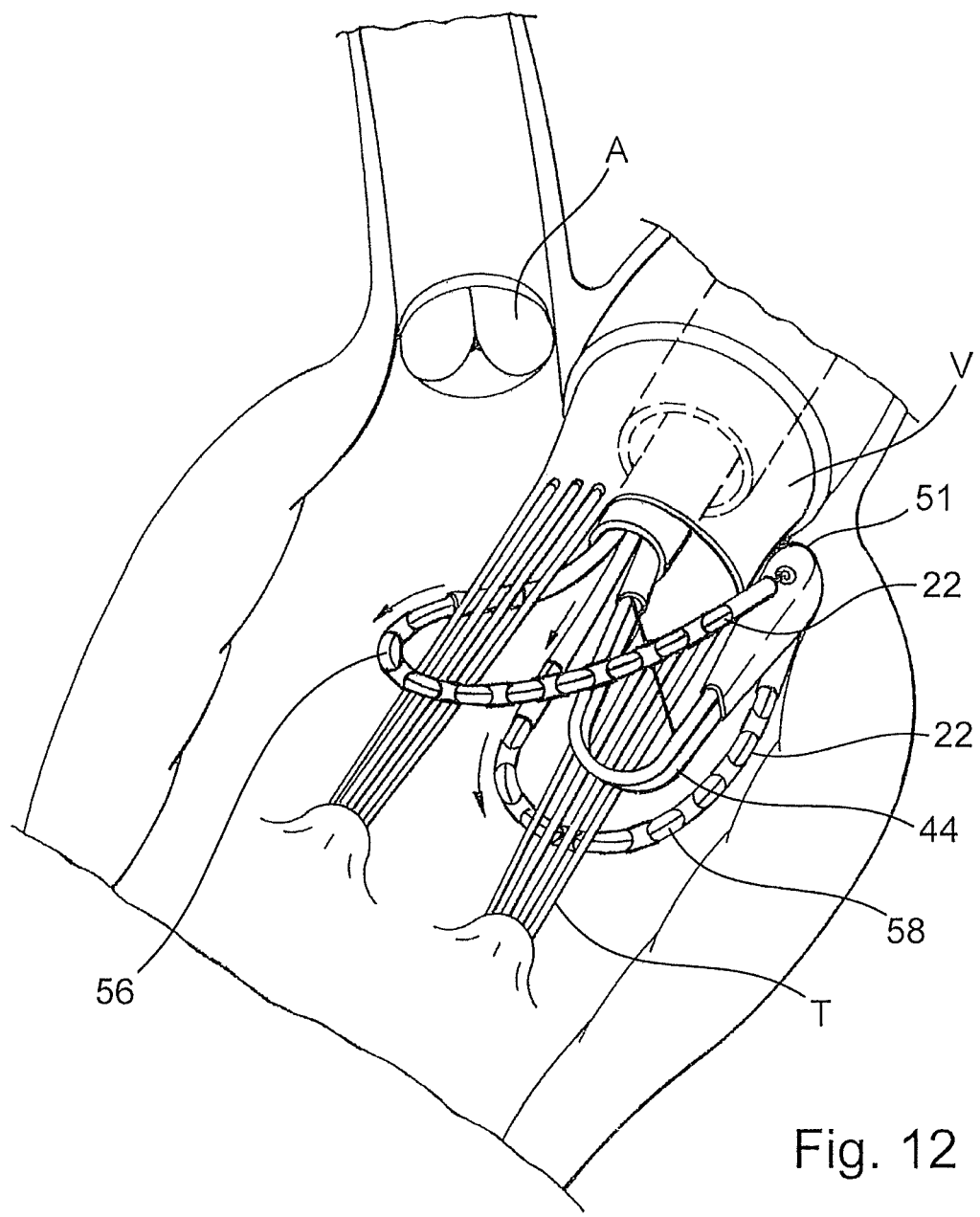
FIG. 12 shows a step of the procedure for implanting the heart prosthesis, in which the sub-components of the containment portion of the heart prosthesis are inserted.
Figure 16:
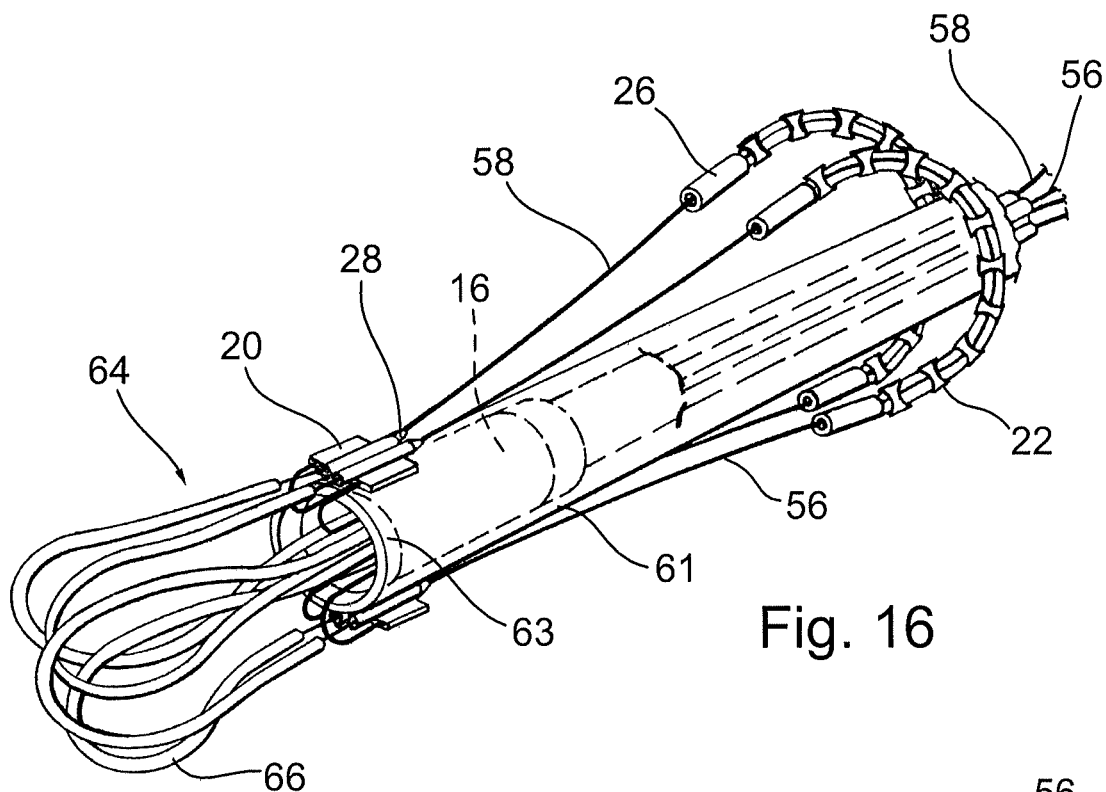
FIG. 16 shows a step of the procedure for implanting the heart prosthesis, in which the central body is advanced.

Now with reference to FIG. 12, the first catheter 40 and the second catheter 44 are preferably left in position in this step in order to facilitate the insertion into the ventricle of the two arcs 22 which constitute the containment portion 18 of the heart prosthesis 10. The two arcs are inserted over the wire, that is to say by sliding on the guidewires. In other words, there is used a longitudinal channel which extends through one of the two arcs in order to insert therein the end 57 of the guidewire 56 which has just been recovered; similarly, the end of the guidewire 58 is inserted into the longitudinal channel which extends through the other arc. Both the arcs 22 are then pushed until they are out of the first catheter 40 and inside the heart. The arcs 22 are pushed until being in contact with the tip 51 of the second catheter 44. At this point, the first catheter 40 and the second catheter 44 can be removed.

It is preferable to leave the main catheter 32 in position and to use it for subsequently introducing therein a device 60 for implanting a heart prosthesis, in which a central body 16 is inserted. The removal of the main catheter 32 or the replacement thereof with another catheter is not excluded in any case.

The device 60 for implanting a heart prosthesis, the details of which can be seen in FIGS. 13, 14 and 15, comprises a catheter 61, through which there are inserted all the other elements as well as the central body 16 of the prosthesis.

The device for implanting a heart prosthesis further comprises a release device 62 for the central body 16 of the prosthesis. The release device 62 is suitable for being inserted into a catheter in order to advance therein the central body 16 of the prosthesis. The device 60 for implanting a heart prosthesis further comprises a device 64 for assisting the connection operation between the central body 16 and the sub-components of the containment portion 18. This assistance device 64 comprises an assembly of catheters 66, of which there are at least two for each arc of the containment portion that are grouped together in the same sheath 68 which partially covers the catheters and leaves at least one free end 70 for each catheter.

In the preferred case depicted, in which the prosthesis comprises two arcs 22, the assistance device 64 comprises four catheters 66. Naturally, if the prosthesis were to comprise a single sub-component of the containment portion 18, two catheters would be sufficient. If, however, the prosthesis comprises three or more sub-components, six or more catheters will be provided.

The catheters 66 are incompressible in the longitudinal direction and are flexible. Furthermore, they are fixed inside the sheath 68 so that they do not slide with respect to each other. Preferably, the sheath 68 further comprises a free longitudinal lumen 72 in which a guidewire can slide if it is advantageous.

Turning now to the implantation procedure for the heart prosthesis 10, for each arc 22 of the containment portion 18 there are inserted the two ends of the guidewire 56, 58 which extend through them, in a corresponding pin 28 of the two connecting elements 20 and then in the catheters 66 of the assistance device 64. For example, the guidewire 56 runs through, in order, a first catheter 66, a first pin 28 of a first connecting element 20, an arc 22, a first pin 28 of the other connecting element 20 and a second catheter 66, as can be seen in FIG. 13.

The catheter 61 is then forced to advance inside the main catheter 32 and through the mitral valve until the end 63 thereof is inside the left ventricle. Although, for greater clarity, FIGS. 16 to 19 show only the devices, the operations shown therein are normally carried out inside the heart of the patient.

The central body 16 is then pushed so that it advances further inside the catheter 61 until the connecting elements 20 are released from the catheter. It may be noted that, when the central body 16 is in a collapsed configuration, in order to be able to slide inside the catheter, the connecting elements are deformed. However, they are constructed from a shape-memory material so that, once they are out of the catheter, they immediately take up the intended configuration.

Figure 17:
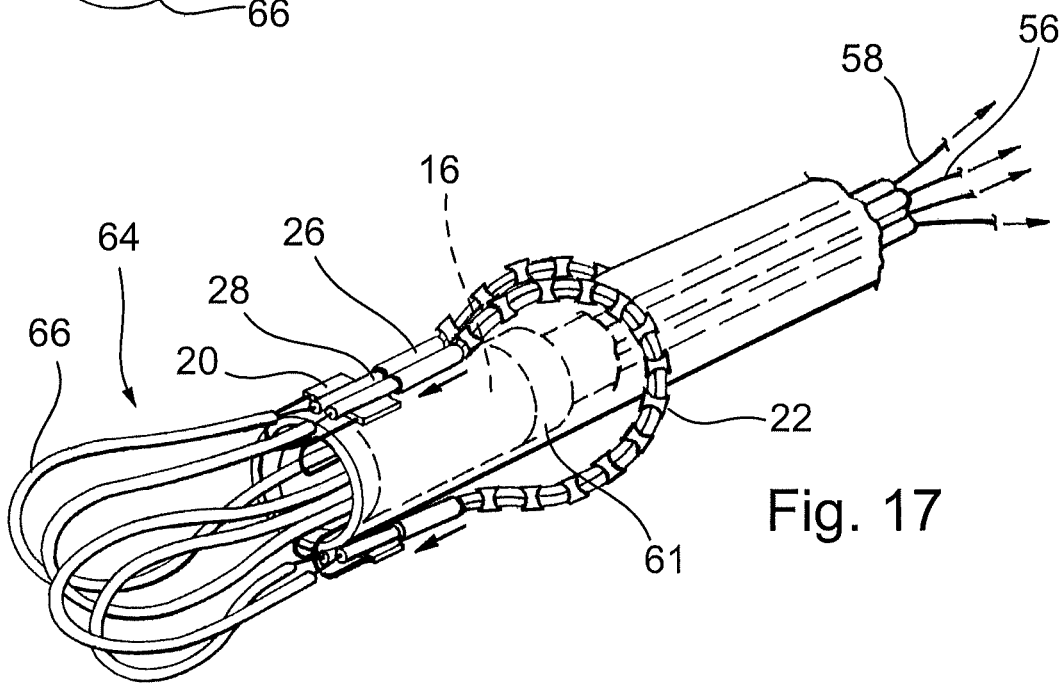
FIG. 17 shows a step of the procedure for implanting the heart prosthesis, in which the central body and the sub-components of the containment portion are connected.

In order to join the central body 16 and the containment portion 18, or in other words to engage the arcs 22 with the connecting elements 20, it is now enough to pull the ends of each guidewire (FIG. 17). In this manner, the pins 28 of the connecting elements 20 are inserted into the axial holes 27 of the engagement portions 26 which are positioned at the ends of the arcs 22. It may be noted that, for tightening, the presence of the assistance device 64 is of primary importance, and in particular of the catheters 66. In fact, the incompressible catheters 66 allow the guidewires to be pulled without kinking against the edge of the catheter 61. In other words, the catheters allow a transfer of a traction force, which otherwise could not be applied, to the portion of guidewire inside each arc which is sufficient to connect to each other the arcs 22 and the connecting elements 20.

Figure 18:
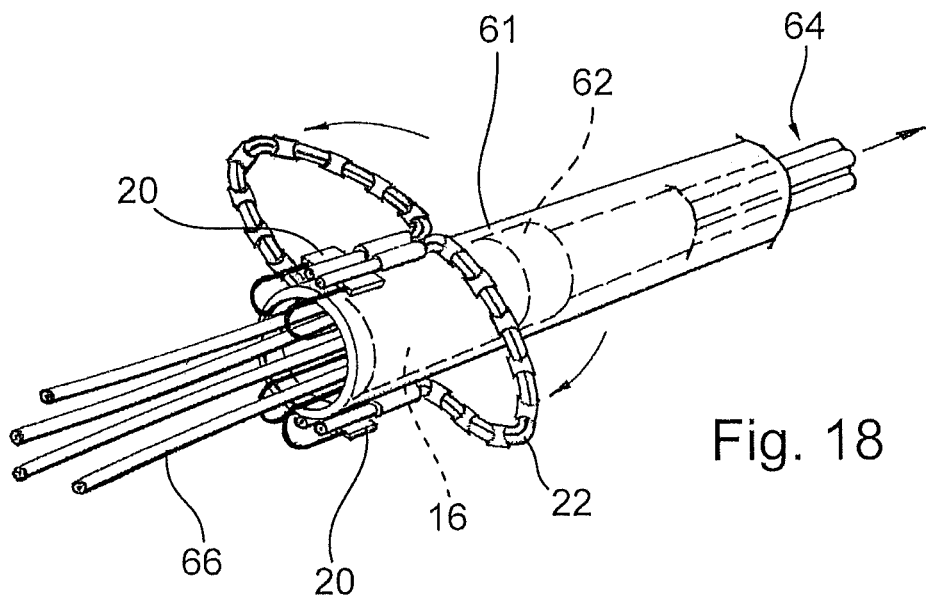
FIG. 18 shows a step of the procedure for implanting the heart prosthesis, in which the device for assisting is removed.

Once the components of the prosthesis are secured to each other, the guidewires can be retrieved as well as the assistance device 64 (FIG. 18).

Figure 19:
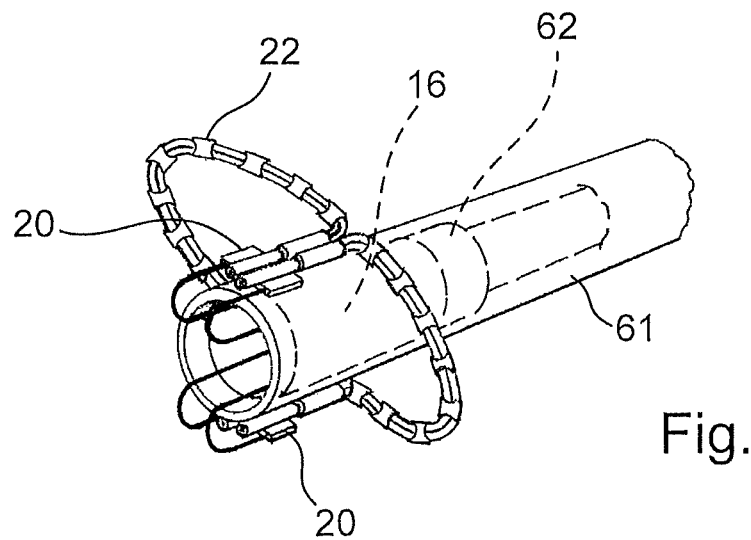
FIG. 19 shows the heart prosthesis in a configuration ready for release in situ.
Figure 20:
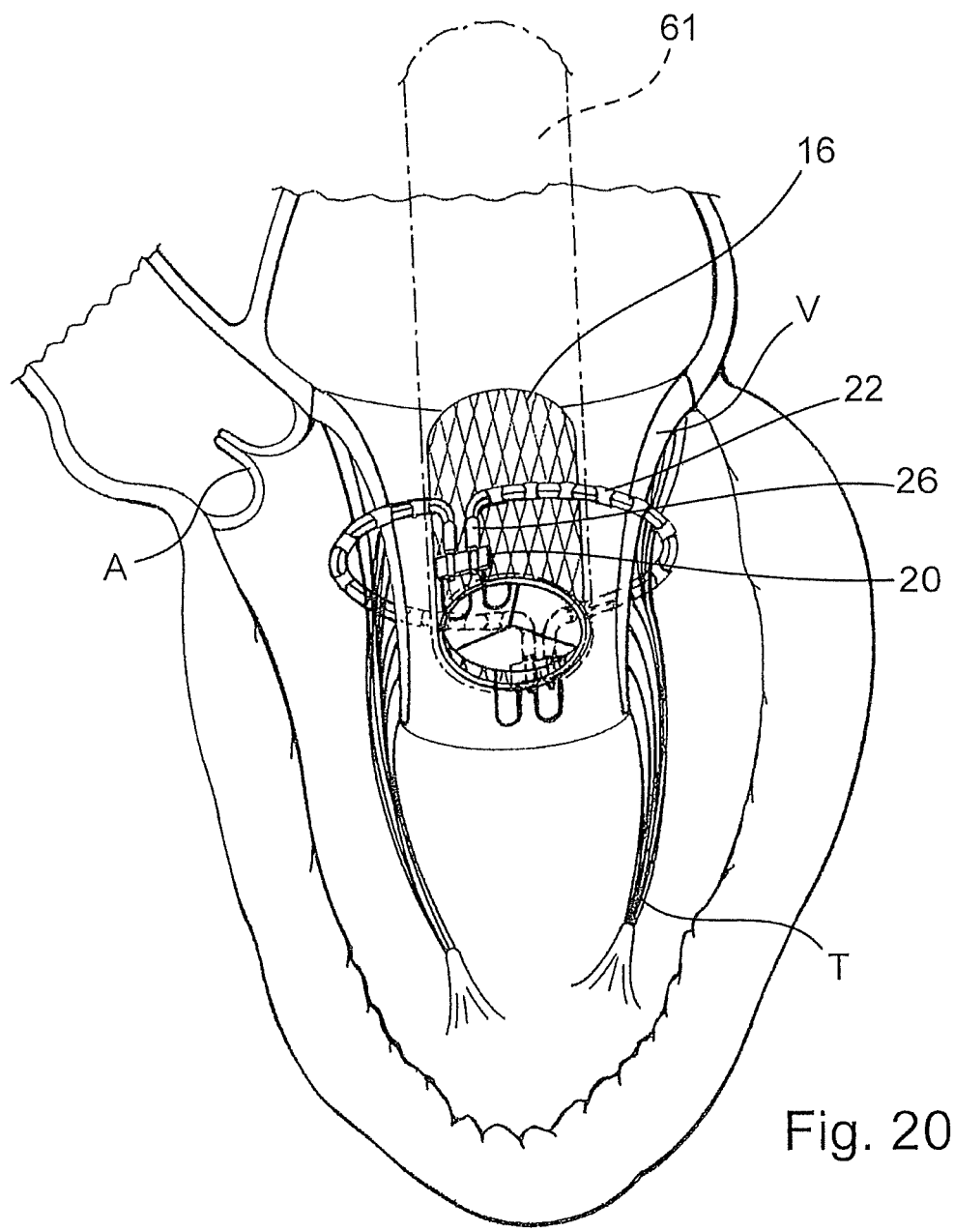
FIG. 20 shows the heart prosthesis ready for release in situ, illustrated in the heart.

Thus, the prosthesis is assembled and maintained in the correct position with the central body 16 still inside the catheter 61 and the two arcs 22 correctly orientated relative to each other so as to constitute the containment portion 18 of the prosthesis (FIGS. 19 and 20).

Figure 21:
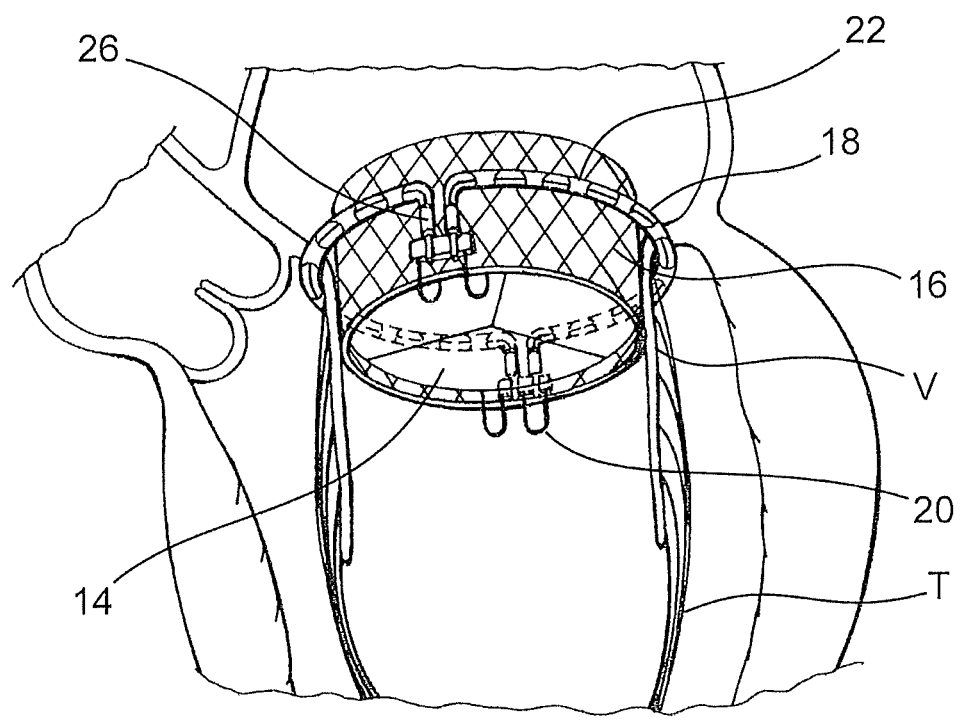
FIG. 21 shows the heart prosthesis in a correctly positioned state.

By acting on the release device 62 and on the catheter 61, the central body 16 of the prosthesis is forced to advance inside the catheter 61 while at the same time the catheter 61 is withdrawn. The central body is maintained substantially in a stable position inside the heart so that the containment portion 18 does not lose contact with the annulus of the native valve while the catheter 61 is retrieved. The central body 16, when it is released from the catheter 61, expands inside the native valve until it is constrained by the containment portion 18 (FIG. 21). The leaflets of the native valve thus remain captured between the central body of the heart prosthesis and the containment portion 18. This configuration brings about a stable and secure positioning of the prosthesis.

All that has been described above must naturally be understood to be one possible embodiment of the invention but not the only one. In an exemplary manner, there will now be described some variants of the objects described above. It should nevertheless be understood that this is not an exhaustive listing of the possible variants.

According to a variant of the invention, a second catheter 244 and a third catheter 245, visible in cross-section in FIG. 22, slide inside the first catheter 40 of the guidewire introducer device 36. The second catheter 244 provides two lumens 46 and 48, suitable for having guidewires sliding therein. The catheter 244, unlike the second catheter 44 described above, has a D-shaped cross-section. Preferably, the second catheter 244 provides an additional lumen 250 for the passage of the wire 52 of the deflection system of the distal portion of the catheter.

The third catheter 254 also has two lumens 45a, 45b, suitable for accommodating two guidewire capturing devices 47. The third catheter 245 also has a D-shaped cross-section which complements the cross-section of the second catheter 244. In this manner, the correct mutual orientation between the catheter 244 and the catheter 245 is ensured, and therefore between the guidewires which are inserted in the lumens 46 and 48 and the guidewire capturing devices 47. Easier positioning of the guidewires around the annulus is thereby allowed.

In this regard, it is evident that the D shape is intended to be understood to be exemplary: it is sufficient for the cross-sections of the two catheters 244 and 245 to be such as to ensure the retention of the correct mutual orientation. For example, the cross-sections of the two catheters 244 and 245 are mutually complementary inside the catheter 40 (in other words, the two cross-sections juxtaposed correspond to the cross-section of the first catheter 40 of the guidewire introducer device 36) and the two catheters 244 and 245 comprise at least one planar abutment face 270 and 272, respectively. It will be understood that the catheters 244 and 245 can slide independently inside the first catheter 40. It is further possible to provide a single lumen 45a.

The third catheter 245 further has an additional lumen 260 for the passage of a wire of a deflection system of the distal portion of the catheter.

With reference now to FIGS. 23 to 26, a second catheter 344 and a third catheter 345 may comprise mechanically bendable metal structures. These metal structures constitute the lumens 346 and 348 of the second catheter 344 and the lumens 345a, 345b of the third catheter 345. Each lumen 346 and 348 has a wire 352 which allows it to be bent. Preferably, each lumen 346 and 348 may form two curves. A first curve is greater than 90°, preferably between 120° and 180°; a second curve is approximately 90°. Preferably, the two curves lay in two mutually perpendicular planes. The two curves are obtained by means of respective portions 354 and 356 which are suitably perforated in order to create anisotropic sections which advantageously ensure a precise and unambiguous orientation of the lumens. This variant further allows straightening of all the lumens before removal of the second and third catheters. In this manner, the friction is greatly reduced, both in relation to the catheter 40, in which the catheters 344 and 345 slide, and in relation to the guidewires which slide therein, making it easier and faster to withdraw the second and third catheters. Furthermore, the metal lumens have a thickness which is particularly small.

The catheters 344 and 345 slide inside the catheter 40 in a straightened configuration (FIG. 24). When they are externalized from the catheter 40, the deflection is then activated so as to curve the portions 354 and to produce the first curves (FIG. 25). The distal deflection of the portions 356 is then activated in order to produce the second curves (FIG. 26). In a generally similar manner, the deflection on the lumens 345a and 345b of the third catheter is also activated. At the end of the operations for positioning the guidewires, all the lumens are straightened (FIG. 24) for the extraction thereof.

Naturally, the principle of the invention remaining the same, the forms of embodiment and details of construction may be varied widely with respect to those described and illustrated, without thereby departing from the scope of the invention.

The invention claimed is:

1. A set for assembling a heart prosthesis, the set comprising:
   a heart prosthesis, comprising an expandable central body, a containment portion having one or more sub-components and limiting, when assembled, an expansion of the central body, and connecting elements provided on the central body for connecting the sub-components of the containment portion to the central body; and
   a connection device for connecting the connecting elements on the central body and the sub-components of the containment portion, said connection device comprising an assembly of catheters, of which there are at least two catheters for each sub-component of the containment portion, the catheters being joined to each other over a portion thereof and each having at least one free end.

2. The set according to claim 1, wherein the catheters which constitute the assembly of catheters are incompressible in a longitudinal direction.

3. The set according to claim 1, wherein the catheters which constitute the assembly of catheters are flexible.

4. The set according to claim 1, wherein the catheters which constitute the assembly of catheters are grouped together in a same sheath which groups together the catheters along a portion thereof.

5. The set according to claim 4, wherein the sheath further comprises a longitudinal lumen.

6. The set according to claim 1, wherein there are at least two sub-components of the containment portion and there are at least four catheters of the assembly of catheters.

7. A set for implanting a heart prosthesis, the set comprising:
 a heart prosthesis, comprising an expandable central body, a containment portion having one or more sub-components limiting, when assembled, an expansion of the central body, and connecting elements provided on the central body for connecting the sub-components of the containment portion to the central body;
 a release device for the central body which is capable of being inserted into a catheter; and
 a connection device for connecting the connecting elements on the central body and the sub-components of the containment portion, said connection device comprising an assembly of catheters, of which there are at least two catheters for each sub-component of the containment portion, the catheters being joined to each other over a portion thereof and each having at least one free end.

8. The set according to claim 7, wherein the catheters which constitute the assembly of catheters are incompressible in a longitudinal direction.

9. The set according to claim 7, wherein the catheters which constitute the assembly of catheters are flexible.

10. The set according to claim 7, wherein the catheters which constitute the assembly of catheters are grouped together in a same sheath which groups together the catheters along a portion thereof.

11. The set according to claim 10, wherein the sheath further comprises a longitudinal lumen.

12. The set according to claim 7, wherein there are at least two sub-components of the containment portion and there are at least four catheters of the assembly of catheters.

* * * * *